(12) United States Patent
Park et al.

(10) Patent No.: US 11,607,157 B2
(45) Date of Patent: Mar. 21, 2023

(54) FLEXIBLE TRANSCUTANEOUS OXYGEN PARTIAL PRESSURE SENSOR

(71) Applicant: A-sen Company, Jeollabuk-do (KR)

(72) Inventors: Jin-woo Park, Seoul (KR); Chang-jin Lim, Seoul (KR)

(73) Assignee: A-sen Company, Jeollabuk-do (KR)

( * ) Notice: Subject to any disclaimer, the term of this patent is extended or adjusted under 35 U.S.C. 154(b) by 167 days.

(21) Appl. No.: 17/112,805

(22) Filed: Dec. 4, 2020

(65) Prior Publication Data

US 2022/0061714 A1    Mar. 3, 2022

(30) Foreign Application Priority Data

Sep. 1, 2020 (KR) .......................... 10-2020-0110966

(51) Int. Cl.
*A61B 5/145* (2006.01)
*A61B 5/00* (2006.01)

(52) U.S. Cl.
CPC ........ *A61B 5/14542* (2013.01); *A61B 5/0059* (2013.01); *A61B 2562/0247* (2013.01); *A61B 2562/18* (2013.01)

(58) Field of Classification Search
CPC .............. A61B 5/14542; A61B 5/0059; A61B 2562/0247; A61B 2562/18;
(Continued)

(56) References Cited

U.S. PATENT DOCUMENTS

| | | | |
|---|---|---|---|
| 2007/0172392 A1* | 7/2007 | Sen .................... | A61B 5/14556 422/82.08 |
| 2015/0182166 A1* | 7/2015 | Evans ................ | A61B 5/14556 600/344 |

(Continued)

FOREIGN PATENT DOCUMENTS

| | | |
|---|---|---|
| JP | 2004515274 A | 5/2004 |
| JP | 2015530888 A | 10/2015 |

(Continued)

OTHER PUBLICATIONS

Yuta Katayama, Yuta Fuijoka, Kosuke Tsukada, "Development of a Patch-Type Flexible Oxygen Partial Pressure Sensor", Jun. 2020, Advanced and intelligent technology for Dementia, vol. 8 (Year: 2020).*

(Continued)

*Primary Examiner* — Eric F Winakur
*Assistant Examiner* — Abid A Mustansir
(74) *Attorney, Agent, or Firm* — McCoy Russell LLP

(57) ABSTRACT

Provided is a flexible transcutaneous oxygen partial pressure sensor which may be closely attached to a skin, be used repeatedly for a long time, and have a highly reliable measurement value.

The flexible transcutaneous oxygen partial pressure sensor of the present disclosure includes: an oxygen sensing film having one surface in contact with a skin; a light detecting portion including a light emitting portion which is positioned above a surface opposite to the one surface of the oxygen sensing film and includes a micro-light emitting diode (LED (μ-LED)), and a light-receiving portion which includes an organic-photodiode (OPD); and a heater portion positioned between the oxygen sensing film and the light detecting portion, and supplying thermal energy to the skin in contact with the oxygen sensing film.

14 Claims, 9 Drawing Sheets

(58) Field of Classification Search
CPC . A61B 5/14552; A61B 5/6826; A61B 5/1491; A61B 5/6833; A61B 2562/164; A61B 2562/0233; A61B 5/6829; A61B 5/6824
See application file for complete search history.

(56) References Cited

U.S. PATENT DOCUMENTS

| 2016/0135723 | A1* | 5/2016 | Kahlman | A61B 5/14552 600/323 |
| 2017/0337412 | A1* | 11/2017 | Bhat | H04N 5/2256 |
| 2019/0313954 | A1* | 10/2019 | Yoo | H01L 51/0097 |
| 2020/0091450 | A1* | 3/2020 | Kim | H01L 31/0256 |

FOREIGN PATENT DOCUMENTS

| JP | 2018526636 A | 9/2018 |
| JP | 6409980 B2 | 10/2018 |
| KR | 20160017601 A | 2/2016 |
| KR | 20160088127 A | 7/2016 |
| KR | 20170004607 A | 1/2017 |

OTHER PUBLICATIONS

Juhyung Park, Dongjun Han, Seunghwan Choi, Yunkyun Kim, Jeonghun Kwak, "Flexible transparent film heaters using a ternary composite of silver nanowire, conducting polymer, and conductive oxide", 2019, Royal Society of Chemistry, vol. 9 (Year: 2019).*

* cited by examiner

FLEXIBLE TRANSCUTANEOUS OXYGEN PARTIAL PRESSURE SENSOR

CROSS-REFERENCE TO RELATED APPLICATION

The present application claims priority to Korean Patent Application No. 10-2020-0110966, filed on Sep. 1, 2020. The entire contents of the above-identified application is hereby incorporated by reference for all purposes.

TECHNICAL FIELD

The following disclosure relates to a flexible transcutaneous oxygen partial pressure sensor, and more particularly, to a flexible transcutaneous oxygen partial pressure sensor which may be closely attached to a skin, be used repeatedly for a long time, and have a highly reliable measurement value.

BACKGROUND

Various types of devices detecting biometric information are being developed as interest in health is increased. In particular, a device specialized for healthcare is being developed as various wearable devices that may be worn directly on a subject become popular.

A method of detecting the biometric information may be roughly divided into invasive and non-invasive methods, and much preferred is the non-invasive method that may simply detect the biometric information while not causing pain in the subject.

Oxygen partial pressure in the body, which is one of the important biometric information may be measured by a transcutaneous oxygen ($TCPO_2$) measurement method. The transcutaneous oxygen ($TCPO_2$) measurement method is the non-invasive method that measures the oxygen partial pressure of a tissue under the skin, and may measure the oxygen partial pressure much more accurately than a laser Doppler method that indirectly predicts the oxygen partial pressure by measuring blood flow velocity and an oximetry method that measures the oxygen partial pressure by using hemoglobin blood saturation. This measurement method may be applied to a patient who is being cured after glass flap surgery performed to heal chronic wounds such as skin necrosis and burns, or a patient who has wounds, focal ischemic vascular disease or diabetic foot disease, and may make it possible to determine a wound treatment evaluation, a vascular disease examination, vasodilation and remodeling evaluations, an amputation range prediction, etc.

In this regard, disclosed are Korean Patent Laid-Open Publication No. 10-2016-0088127 entitled 'Apparatus for detecting information of the living body' and Korean Patent Application Laid-Open Publication No. 10-2017-0004607 entitled 'Apparatus and method for detecting biometric information.

The above-described conventional apparatuses for detecting biometric information attempt to measure the biometric information (e.g., oxygen partial pressure) using an optical signal based on a flexible material. However, this non-invasive method is an oximetry-based measurement method, which uses a principle of indirectly measuring hemoglobin oxygen saturation, and thus fails to represent oxygen partial pressure of the tissue or skin surface. In addition, most of the subjects each show the value of 90% or more regardless of their diseases, and this measurement method usually has the accuracy of ±1-2%. Therefore, it is difficult to accurately determine the severity of the disease.

In addition, the conventional apparatuses for detecting biometric information fail to sufficiently deliver oxygen near the skin and region of interest to a sensor through an epidermal layer of the skin, and thus show the oxygen partial pressure measured lower than an expected value. Therefore, a highly reliable result cannot be expected from these apparatuses.

RELATED ART DOCUMENT

Patent Document

Korean Patent Laid-Open Publication No. 10-2016-0088127
Korean Patent Laid-Open Publication No. 10-2017-0004607

SUMMARY

An embodiment of the present disclosure is directed to providing a flexible transcutaneous oxygen partial pressure sensor which may have flexibility, be used repeatedly for a long time, and have a highly reliable measurement value.

In one general aspect, a flexible transcutaneous oxygen partial pressure sensor includes: an oxygen sensing film having one surface in contact with a skin; a light detecting portion including a light emitting portion which is positioned above a surface opposite to the one surface of the oxygen sensing film and includes a micro-light emitting diode (LED (µ-LED)), and a light-receiving portion which includes an organic-photodiode (OPD); and a heater portion positioned between the oxygen sensing film and the light detecting portion, and supplying thermal energy to the skin in contact with the oxygen sensing film.

In the flexible transcutaneous oxygen partial pressure sensor according to an embodiment of the present disclosure, the heater portion may include a transparent conductor generating Joule heat.

In the flexible transcutaneous oxygen partial pressure sensor according to an embodiment of the present disclosure, the heater portion may include a transparent conductive oxide.

In the flexible transcutaneous oxygen partial pressure sensor according to an embodiment of the present disclosure, the heater portion may have a thickness of 10 µm to 100 µm.

In the flexible transcutaneous oxygen partial pressure sensor according to an embodiment of the present disclosure, the heater portion may heat the skin in contact with the oxygen sensing film to a temperature of 40° C. to 50° C. In the flexible transcutaneous oxygen partial pressure sensor according to an embodiment of the present disclosure, the light detecting portion may include the light emitting portion stacked on the heater portion and the light-receiving portion stacked above the light emitting portion, and may further include an optical filter positioned between the light emitting portion and the light-receiving portion.

In the flexible transcutaneous oxygen partial pressure sensor according to an embodiment of the present disclosure, the light emitting portion may include a transparent substrate and an array in which the micro-LEDs are arranged on the transparent substrate, the transparent substrate being made of a flexible light-transmitting material.

In the flexible transcutaneous oxygen partial pressure sensor according to an embodiment of the present disclosure, the organic-photodiode (OPD) may include an electron transport layer including polyethyleneimine ethoxide and cesium carbonate.

In the flexible transcutaneous oxygen partial pressure sensor according to an embodiment of the present disclosure, the electron transport layer may have a first region including polyethyleneimine ethoxide and a second region doped with the first region and including cesium carbonate.

The flexible transcutaneous oxygen partial pressure sensor according to an embodiment of the present disclosure may further include an oxygen blocking film positioned between the oxygen sensing film and the heater portion, and having light transmittance.

In the flexible transcutaneous oxygen partial pressure sensor according to an embodiment of the present disclosure, the oxygen blocking film may include polyvinylidene chloride.

The flexible transcutaneous oxygen partial pressure sensor according to an embodiment of the present disclosure may further include a light shielding portion stacked on the light detecting portion and blocking light.

In the flexible transcutaneous oxygen partial pressure sensor according to an embodiment of the present disclosure, the oxygen sensing film may contain a polymer matrix, a phosphor and a scattering material.

In the flexible transcutaneous oxygen partial pressure sensor according to an embodiment of the present disclosure, the scattering material may include a titanium dioxide particle.

In the flexible transcutaneous oxygen partial pressure sensor according to an embodiment of the present disclosure, the titanium dioxide particle may have a rutile structure.

DETAILED DESCRIPTION

Figure 1:
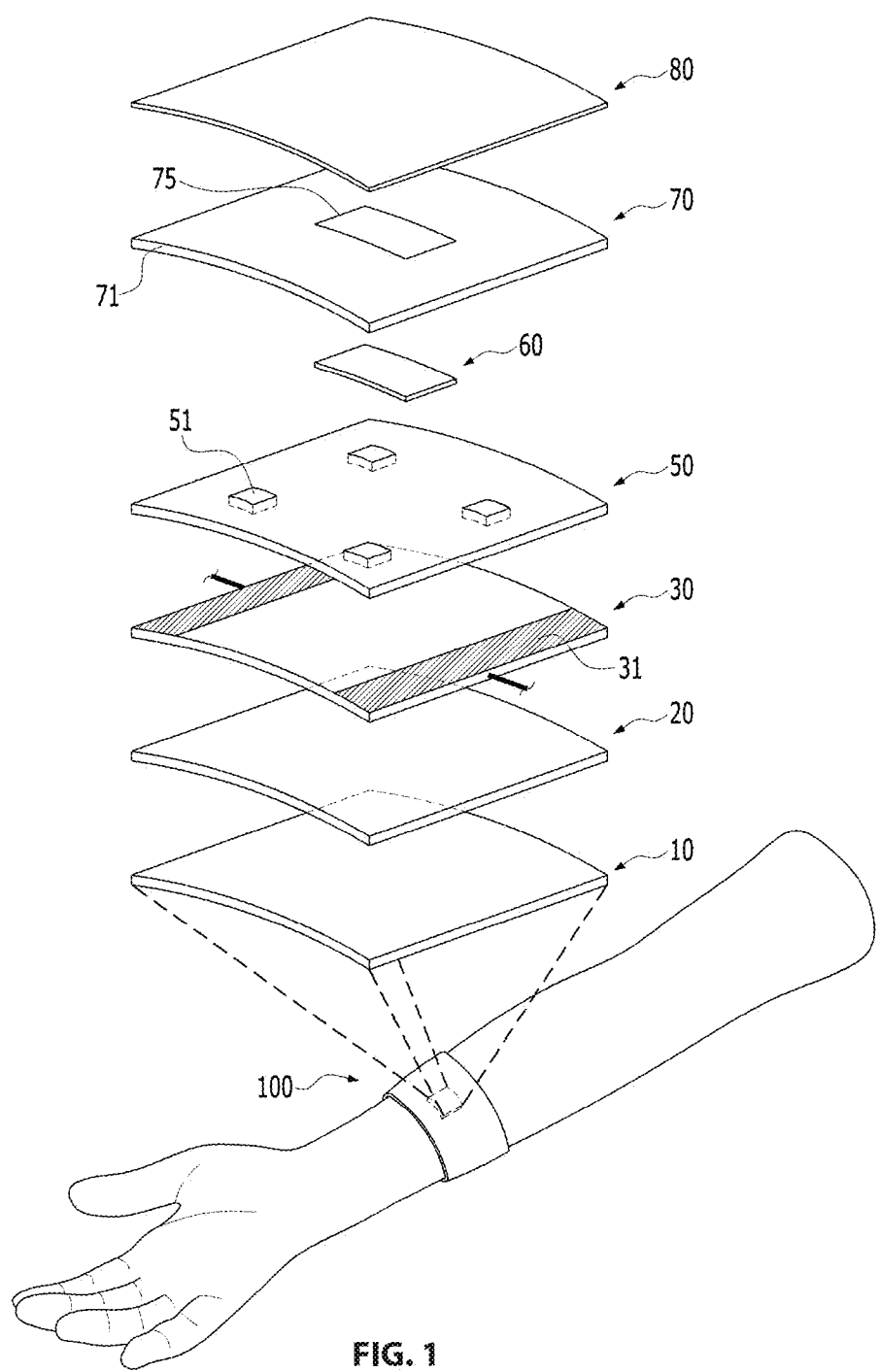
FIG. 1 is an exploded perspective view showing a flexible transcutaneous oxygen partial pressure sensor according to an embodiment of the present disclosure.

Technical terms and scientific terms used in the present specification have the general meaning understood by those skilled in the art to which the present disclosure pertains unless otherwise defined, and a description for the known function and configuration unnecessarily obscuring the gist of the present disclosure is omitted in the following description and the accompanying drawings.

In addition, singular forms used in the present specification are intended to include plural forms unless otherwise indicated in the context.

In addition, a unit used in the present specification is based on weight. For example, the unit of % or ratio refers to wt % or weight ratio, and wt % refers to weight ratio of a certain component in a total composition, unless otherwise defined.

In addition, a numerical range used in the present specification includes the lower and upper limits and all values within the range, an increment logically derived from the shape and width of the defined range, all of the values defined therein and all possible combinations of the upper and lower limits in the numerical range defined in a different shape. The defined numerical range also includes a value outside the numerical range, which may be generated due to an experimental error or rounding of the value unless otherwise specified in the specification of the present disclosure.

The term 'to include' in the present specification is a comprehensive description that has the meaning equivalent to an expression such as 'to provide', 'to contain', 'to have' or 'to be featured', and does not exclude an element a material or a process, which is not additionally listed.

In the present specification and appended claims, when a portion such as a film (layer), region, component or the like is referred to as being 'on' another portion, it indicates not only a case where the corresponding portion is directly on the another portion, but also a case where another film (layer), another region and another component are interposed therebetween.

A flexible transcutaneous oxygen partial pressure sensor according to the present disclosure includes: an oxygen sensing film having one surface in contact with a skin; a light detecting portion including a light emitting portion which is positioned above a surface opposite to the one surface of the oxygen sensing film and includes a micro-light emitting diode (LED (μ-LED)), and a light-receiving portion which includes an organic-photodiode (OPD); and a heater portion positioned between the oxygen sensing film and the light detecting portion, and supplying thermal energy to the skin in contact with the oxygen sensing film.

A conventional transcutaneous oxygen partial pressure sensor may measure oxygen partial pressure using an optical signal. In particular, a band-type transcutaneous oxygen partial pressure sensor may include a sensing film made of flexible material, an organic light emitting diode (OLED)-based light emitting portion positioned above the sensing film, and a light detecting portion including a photodiode. Therefore, when attached to the skin, the sensor may be closely and completely attached to the curved skin unlike an existing transcutaneous oxygen partial pressure sensor made of a hard material, and may perform higher-accuracy sensing than the existing transcutaneous oxygen partial pressure sensor made of the hard material. However, such a conventional band-type transcutaneous oxygen partial pressure sensor is difficult to repeat measurements for a long time because its light source is based on the OLED and thus vulnerable to heat, and very unstable at room temperature. In addition, the conventional sensor fails to sufficiently deliver oxygen in the blood to the sensor through an epidermal layer of the skin, and thus shows the oxygen partial pressure measured lower than an expected value. Therefore, a highly reliable result cannot be expected from this sensor.

However, the sensor of the present disclosure may use a micro-LED as its light source, and include the heater portion supplying thermal energy to the skin in contact with the oxygen sensing film, and may thus measure the oxygen partial pressure repeatedly for a long time and increase the reliability of the measurement value. In detail, the sensor of the present disclosure may heat the skin whose oxygen partial pressure to be measured using the heater portion positioned between the oxygen sensing film and the light detecting portion, increase the blood flow flowing under the heated skin, and increase the partial pressure of oxygen delivered to the oxygen sensing film. Therefore, the sensor of the present disclosure may more accurately sense the oxygen partial pressure. Here, the sensor of the present disclosure may use the micro-LED as its light source, thereby preventing the life of the light source from being decreased due to heat generated in the heater portion and heat caused by the operation of the light source, and may reliably measure the oxygen partial pressure repeatedly for a long time despite the heat generated in the heater portion and the light source.

FIG. 1 shows an embodiment of the present disclosure.

Referring to FIG. 1, the present disclosure includes: an oxygen sensing film 10; a heater portion 30; and a light detecting portion, and may further include: an oxygen blocking film 20 positioned between the oxygen sensing film 10 and the heater portion 30; and a light shielding portion 80 stacked on the light detecting portion. The flexible transcutaneous oxygen partial pressure sensor 100 of the present disclosure may be manufactured in various sizes and shapes based on measurement conditions such as a patient's measurement portion, age, etc.

In detail, the oxygen sensing film 10 may be attached to the skin of a subject to be measured, and the subject to be measured may be a human being or an animal. The oxygen sensing film 10 is for sensing oxygen delivered from the skin, and may sense oxygen with high sensitivity because the film contains a polymer matrix, a phosphor and a scattering material.

The polymer matrix is the base of the oxygen sensing film, and may be made of a flexible material to be closely attached to the skin. The polymer matrix may be formed by more than one type of polymer. In detail, the polymer may be an acrylic polymer, a siloxane polymer, a vinyl polymer, a urethane polymer, an olefin polymer or a cellulose polymer. As a non-limiting example, the polymer may be any one or a combination of two or more selected from the group consisting of polyacrylonitrile (PAN), polystyrene-co-acrylonitrile (PSAN), polyvinyl alcohol (PVA), polyvinyl methyl ketone (PVMK), polyvinyl chloride (PVC), polymethyl methacrylate (PMMA), polydimethylsiloxane (PDMS), polyhexafluoroisopropyl methacrylate-co-(heptafluoro-n-butyl methacrylate (FIB), poly(isobutyl methacrylate-co-trifluoroethyl methacrylate)[poly(IBM-co-TFEM)], poly(trimethylsilyl propyne) (PolyTMSP), ethyl cellulose (EC), silicone rubbers, polystyrene (PS), cellulose derivatives and poly (hydroxyethyl methacrylate) (pHEMA). However, the present disclosure is not limited to this selection, and may use any polymer capable of forming a polymer matrix by using a flexible material.

The phosphor may be dispersed in the polymer matrix, absorb light emitted from the light emitting portion 50 of the light detecting portion, and react with oxygen. That is, oxygen supplied from the skin may be adsorbed to the phosphor. Therefore, the oxygen sensing film 10 may absorb the light emitted from the light emitting portion 50, and may then emit light of a specific wavelength having a light luminescence (PL) characteristic, which is modified based on oxygen concentration, to the light-receiving portion 70 of the light detecting portion, thereby allowing the sensor to sense the oxygen partial pressure.

The phosphor may be physically, electrically or chemically adsorbed on a surface or inside of the polymer matrix, or may be embedded in the polymer matrix. In detail, the phosphor may include at least one type of fluorescent material that reacts with oxygen. In more detail, the phosphor may be any one or a combination of two or more selected from the group consisting of pyrene, ruthenium(II)-tris(4,7, diphenyl-1,10, phenanthroline) (Ru(dpp)32+), platinum(II)-2, 3, 7, 8, 12, 13, 17, 18-octaethylporphyrin (PtOEP), palladium(II)-2, 3, 7, 8, 12, 13, 17, 18-octaethylporphyrin (PdOEP), platinum(II)-5, 10, 15, 20, tetrakis (2, 3, 4, 5, 6-pentafluorophenyl)porphyrin (PtTFPP), palladium (II)-5,10,15,20-tetrakis(2, 3, 4, 5, 6-penta-fluorophenyl)porphyrin (PdTFPP), platinum(II)-5,10,15,20-tetrakis(2,3,4,5, 6-penta-fluorophenyl)porpholactone (PtTFPL), ruthenium-tris(1,10-phenanthroline) (Ru(phen)32+), ruthenium-tris(2, 2'-bipyridine) (Ru(bpy)32+), ruthenium-bis(2,2':6',2" terpyridine) (Ru(trpy)22+), europium(III)-tris(thenoyltrifluoroacetylacetonato)-(2-(4-diethylaminophenyl)-4,6-bis(3, 5-dimethylpyrazol-1-yl)-1,3,5-triazine) [Eu(tta)3(dpbt)] and 8-hydroxypyrene-1,3,6-trisulfonic acid (HPTS), and is not limited thereto as long as the material is the fluorescent material that reacts with oxygen.

In addition, the phosphor may further include a fluorescent material that may additionally detect any one or two or more materials selected from the group consisting of water and nitrogen monoxide (NO), hydrogen ion concentration (pH), serum, lactate, alcohol and glucose, which are included on the surface and inside of a living body. Therefore, the present disclosure is not limited to oxygen, and may further measure various biometric information on the surface and inside of the living body.

In an aspect of the present disclosure, the phosphor may include a first fluorescent material that is dispersed in the polymer matrix and reacts with an analyte (oxygen partial pressure) and a second fluorescent material that does not react with the analyte. As such, the phosphor may be subjected to color decomposition by the first and second fluorescent materials, and it is possible to use the principle of measuring a ratio metric based on color decomposition.

The scattering material may be dispersed in the polymer matrix in the same manner as the phosphor described above, and may cause multiple scattering when light is emitted from the light source, thereby increasing a probability in which the light is absorbed by the phosphor. That is, the scattering material may increase the intensity of the light emission generated from the sensing film, thereby improving the sensing sensitivity of the sensing film. The scattering material may be physically, electrically or chemically adsorbed on a surface or inside of the polymer matrix, or may be embedded in the polymer matrix.

It is possible to use any scattering material without limitation to specific material and structure as long as the material can scatter light without interfering with the flexibility and light transmittance of the polymer matrix, and the scattering material may preferably be titanium dioxide ($TiO_2$), and specifically, a titanium dioxide particle having a rutile structure. The titanium dioxide as described above may have a high light-scattering effect, thereby enabling highly sensitive oxygen sensing by light correction. The titanium dioxide having such a rutile structure may have a diameter of 10 nm to 500 nm, specifically, 50 nm to 300 nm, and more specifically, 100 nm to 200 nm. The titanium dioxide particle having a diameter in the above range may have a stable rutile structure, and enable more highly sensitive oxygen sensing.

The light detecting portion may be positioned above the surface opposite to the one surface of the oxygen sensing film 10, and may emit and collect light on the oxygen sensing film 10, thereby measuring a change in a photocurrent signal that appears differently depending on the concentration of oxygen adsorbed on the oxygen sensing film 10. The light detecting portion may be positioned on the surface opposite to the one surface of the oxygen sensing film 10, and may include the light emitting portion 50 which includes a micro-LED 51 and the light-receiving portion 70 which includes an organic-photodiode 75.

In an aspect of the present disclosure, the light detecting portion may include the light-receiving portion 70 above the light emitting portion 50 as shown in FIG. 1. In detail, the film-shaped light-receiving portion 70 including a flexible substrate 71 and the organic-photodiode 75 may be stacked on a top surface of the film-shaped light emitting portion 50 including a transparent substrate and an array in which the micro-LEDs 51 are arranged on the transparent substrate.

Alternatively, the light emitting portion 50 and the light-receiving portion 70 may be positioned on the same plane. In detail, the organic-photodiode 75 as well as the micro-LED 51 may be arranged on the transparent substrate.

The positions of the micro-LED 51 and the organic-photodiode 75 of the light detecting portion are not particularly limited as long as the components do not interfere with each other's light emission and collection, and increase the efficiency of the light emission and collection. One light detecting portion including a plurality of micro-LEDs 51 adjacent to one organic-photodiode 75 may preferably be used as one light detecting portion unit, and the light detecting portion may include the one light detecting portion unit or a plurality of light detecting portion units.

Figure 2:
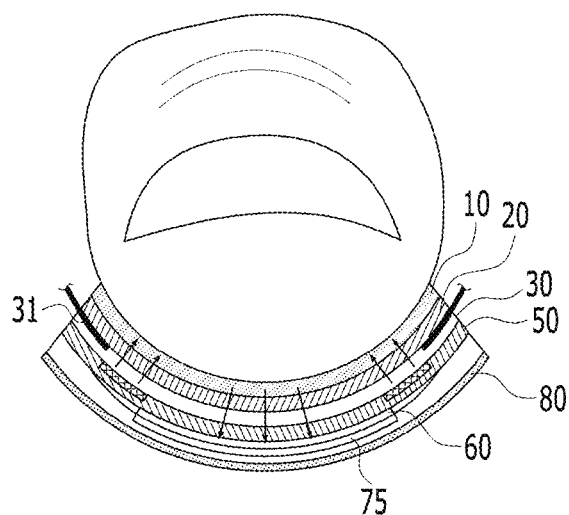
FIG. 2 is a perspective view showing a main portion of the flexible transcutaneous oxygen partial pressure sensor shown in FIG. 1.

The light detecting portion unit may include the one organic-photodiode 75 and the plurality of micro-LEDs 51 each arranged adjacent to a plurality of edges of the organic-photodiode 75. As shown in FIGS. 1 and 2, four micro-LEDs 51 may be respectively positioned at positions adjacent to the four edges of the organic-photodiode 75 formed in a rectangular film shape. The light detecting portion having this structure may have an optimized area of the organic-photodiode 75, that is, an actual area of the light source that emits the light on the sensing film, compared to a light-receiving area, i.e. the area of the micro-LED 51, thereby increasing the light emission efficiency.

In detail, the light emitting portion 50 may be stacked on the heater portion 30 to emit light to the oxygen sensing film 10, and may include the micro-LED 51 (µ-LED) as a light source. The light emitting portion 50 is stronger against heat than the conventional light source, OLED, and may prevent the life of the light source from being decreased due to heat generated by light emission and heat of the heater portion 30, thereby allowing the transcutaneous oxygen partial pressure sensor of the present disclosure to sense transcutaneous oxygen ($TCPO_2$) repeatedly for a long time. The light emitting portion 50 may include one or the plurality of micro-LEDs 51, and is not limited thereto.

In one aspect of the present disclosure, the light emitting portion 50 may include the transparent substrate and the array in which the plurality of micro-LEDs 51 are arranged on the transparent substrate. In detail, the array in which the plurality of micro-LEDs 51 are arranged may be included and inserted into the transparent substrate. As a specific example, the thickness of the transparent substrate may have a value higher than the height of the micro LED, and the micro-LED 51 may be embedded in the transparent substrate. Alternatively, the micro LED may have a portion exposed to the outside and be positioned in the transparent substrate. Here, the thickness of the transparent substrate may have a value lower than the height of the micro LED, and is not limited thereto. The thickness of the transparent substrate may have a value equal to or higher than the height of the micro LED.

The transparent substrate may be made of a flexible light-transmitting material. In detail, the transparent substrate may be made of an acrylic polymer, a siloxane polymer, a vinyl polymer, a urethane polymer, an olefin polymer or a cellulose polymer. As a specific example, the transparent substrate may be made of polydimethylsiloxane (PDMS), and may use all flexible materials having high light transmittance.

The transparent substrate of the light emitting portion 50 may support the plurality of micro-LEDs 51, may be made of the light-transmitting material, and thus does not interfere with the light emission of the light emitting portion 50 or light collection of the light-receiving portion 70 to be described below.

The array of micro-LED 51 may have the plurality of micro-LEDs 51 arranged on the transparent substrate, and in which the micro-LEDs 51 may be arranged not to interfere with the light collection of the organic-photodiode 75 of the light-receiving portion 70 to be described below. The micro-LEDs 51 may be respectively positioned adjacent to edges of the light-receiving area, centering on the light-receiving area of the light-receiving portion 70 to be described below. The micro-LEDs 51 may be positioned to be spaced apart from each other by an equal interval, and are not limited thereto.

In one aspect of the present disclosure, the light emitting portion 50 may further include a switch (not shown) using an element such as a thin film transistor (TFT) to minimize power consumption. The switch may periodically turn on/off supplied power to minimize the power consumption.

The light-receiving portion 70 may be stacked on the light emitting portion 50, and include the organic-photodiode (OPD) 75 that may collect light emitted from the oxygen sensing film 10.

Figure 3:
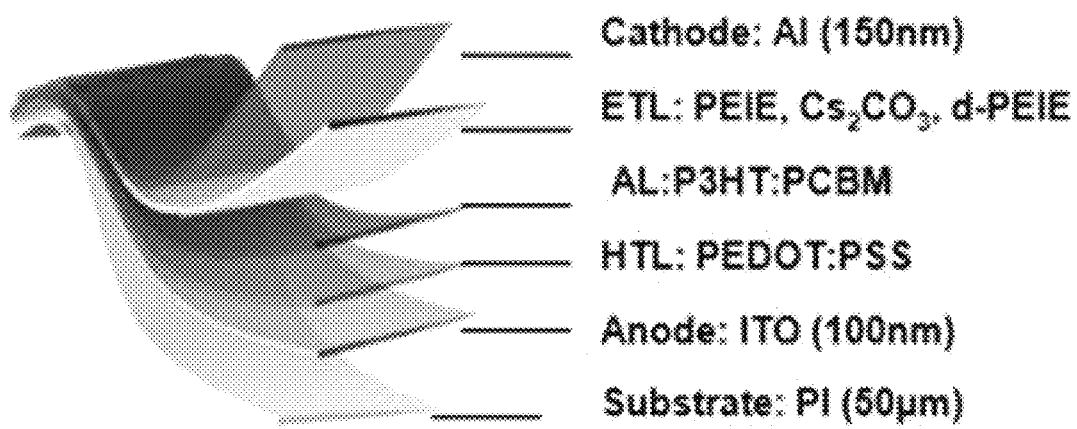
FIG. 3 is a perspective view showing another main portion of the flexible transcutaneous oxygen partial pressure sensor shown in FIG. 1.

FIG. 3 shows an embodiment of the organic-photodiode 75. Hereinafter, the organic-photodiode 75 is described in detail with reference to FIG. 3.

As shown in the drawing, the organic-photodiode 75 may include an insulating substrate on which an anode layer is positioned, a hole transport layer, an active layer, an electron transport layer and a cathode layer.

The insulating substrate may use transparent glass or a transparent polymer film, and may preferably use a transparent polymer film made of the flexible material.

The anode layer may be made of a transparent conductive metal oxide such as indium tin oxide (ITO), fluorine tin oxide (FTO) or indium zinc oxide (IZO), and is not limited thereto.

The hole transport layer may be positioned on the insulating substrate on which the anode layer is positioned to provide a smooth path for a hole. The hole transport layer may include any one or two or more selected from the group consisting of poly(3,4-ethylenedioxythiophene):poly(styrene sulfonate) (PEDOT:PSS), polyacetylene, polypyrrole, polythiophene and [poly(p-phenylenevinylene)].

The active layer may be positioned on the hole transport layer. The active layer may be made of a mixture of a p-type polymer, for example, a thiophene-based polymer such as ((poly 3-hexylthiophene)) or ((poly3-hexylthiophene-2,5-diyl)), and an n-type polymer in which a polymer is grafted onto a material commonly referred to as 'PCBM' such as (methyl [6,6]-phenyl-C61-butanoate).

The electron transport layer may be positioned on the active layer to provide a smooth path for an electron. The electron transport layer may include titanium oxide (TiOx), tungsten oxide (WOx), zinc oxide (ZnOx), iron oxide (FeOx), copper oxide (CuOx), zirconium oxide (ZrOx), Chromium (CrOx), vanadium oxide (VOx), manganese oxide (MnOx), cobalt oxide (CoOx), nickel oxide (NiOx), tin oxide (SnOx) or iridium oxide (IrOx), which is used for a conventional electron transport layer. However, the electron transport layer may preferably include polyethyleneimine ethoxide (PEIE) and cesium carbonate ($Cs_2CO_3$). In more detail, the electron transport layer may have a first region including polyethyleneimine ethoxide and a second region doped with the first region and including cesium carbonate. The organic-photodiode 75 including such an electron transport layer may have flexibility and high external quantum efficiency (EQE), and may have higher sensitivity than a conventional organic-photodiode 75.

A hole injected from the hole transport layer and an electron injected from the electron transport layer may interact with each other on the active layer, and this interaction may form an exciton, i.e. an electron-hole pair, and the electron and the hole may be separated from each other to generate a photocurrent.

The cathode layer may be positioned on the electron transport layer. The cathode layer may be formed by depositing aluminum on the hole transport layer, and may be formed in a thickness of 50 to 200 nm, specifically, 100 nm to 150 nm. Such an aluminum-based cathode layer may have high electrical conductivity, and thus there is no problem in securing electrical conductivity even when the cathode layer has a thin thickness to be semi-transparent.

As such, the organic-photodiode 75 of the present disclosure may have the opposite electrodes respectively formed to be transparent and semi-transparent, thereby securing a transflective property and showing excellent flexibility and high sensitivity.

In one aspect of the present disclosure, as shown in FIG. 1, the light-receiving portion 70 may include the flexible substrate 71 and the organic-photodiode 75 supported by the flexible substrate 71. In detail, the organic-photodiode 75 may be included and inserted into the flexible substrate 71. In one embodiment, the thickness of flexible substrate 71 may be thicker than the thickness of the organic-photodiode 75, and the organic-photodiode 75 may be embedded in the flexible substrate 71. Here, the flexible substrate 71 may preferably include the light-transmitting material such as polydimethylsiloxane (PDMS) and polymethyl methacrylate (PMMA) not to interfere with the light collection of the organic-photodiode 75. Alternatively, the organic-photodiode 75 may have a portion exposed to the outside and positioned in the flexible substrate 71. Here, the thickness of the flexible substrate 71 is not particularly limited.

The flexible substrate 71 may be made of a flexible material such as an acrylic polymer, a siloxane polymer, a vinyl polymer, a urethane polymer, an olefin polymer or a cellulose polymer. As a specific example, the flexible substrate 71 may be made of polydimethylsiloxane (PDMS), and may be made of all flexible materials.

The organic-photodiode 75 may be formed in a shape of a film, and may have a quadrangle-shape as shown in FIGS. 1 and 2, and is not limited thereto. The organic-photodiode 75 may be positioned in the center of the flexible substrate 71, and may have a smaller area than the flexible substrate 71. The area formed by the organic-photodiode 75 is the light-receiving area in which the light is received, and as described above, the micro-LEDs 51 may be arranged to be adjacent to and spaced apart from each other around the light-receiving area.

In one aspect of the present disclosure, the light detecting portion may further include an optical filter 60 positioned between the light emitting portion 50 and the light-receiving portion 70.

The optical filter 60 is for removing noise by filtering light of a specific wavelength, and may be made of a flexible material. In detail, the optical filter 60 may be a red cellophane optical filter, and may remove noise from green light emitted from the micro-LED 51. Accordingly, it is possible to minimize an interference effect due to noise introduced into the light-receiving portion 70, and prevent signal crosstalk due to noise.

The heater portion 30 may be positioned between the oxygen sensing film 10 and the light detecting portion, and may supply heat energy to the skin in contact with the oxygen sensing film 10, that is, an oxygen partial pressure measurement portion. The heater portion 30 may heat the oxygen partial pressure measurement portion, thereby expanding a blood vessel, increasing a blood flow velocity, and increasing a blood flow amount. Accordingly, a large amount of oxygen may be supplied to the measurement portion, thereby increasing the partial pressure of oxygen discharged from the skin and supplied to the oxygen sensing film 10. In addition, as the epidermal layer of the skin is heated, a lipid layer included in the epidermal layer of the skin may be reversibly softened to reduce the oxygen blocking rate of the epidermal layer, thereby increasing the amount of oxygen discharged from the skin tissue, and further increasing the partial pressure of oxygen supplied to the oxygen sensing film. The sensor including such a heater portion 30 may more accurately measure the oxygen partial pressure, enabling more reliable measurement of the oxygen partial pressure.

In detail, the heater portion 30 may include a transparent conductor generating Joule heat. The heater portion 30 may be made of the transparent conductor not to interfere with the light emission and collection of the light detecting portion, and easily supply and stop the heat energy to the skin depending on whether or not the power is applied, thereby allowing the sensor to have increased efficiency of sensing the oxygen partial pressure. In more detail, the heater portion 30 may be made of a flexible material including a transparent conductive oxide. The heater portion 30 may preferably be made of any one or two or more selected from the group consisting of tin oxide ($SnO_2$), antimony tin oxide (ATO), fluoro tinoxide (FTO), zinc oxide (ZnO), aluminum zinc oxide (AZO), gallium zinc oxide (GZO), boron zinc oxide (BZO), SiO$_2$—ZnO (SZO), indium zinc oxide (In$_2$O$_3$), indium tin oxide (ITO) and indium zinc oxide (IZO). Such a transparent conductive oxide may have a relatively high surface resistance (Rs) compared to a silver nanowire commonly used as a conventional flexible transparent heater, and may reduce a risk of electric shock to a user.

The heater portion 30 may be formed by depositing a thin film of the transparent conductive oxide on a transparent substance. In detail, it is possible to position electrodes on the opposite ends of the thin film of the transparent conductive oxide formed by the deposition and then heat the thin film by applying the power. The transparent substance is a transparent flexible material and may include one or more polymers selected from the group consisting of polyimide (PI), polycarbonate (PC), polyethylene terephthalate (PET), polyethylene naphthalate (PEN), polyether sulfone (PES) and polyvinyl alcohol (PVA), and is not limited thereto.

In one aspect of the present disclosure, the heater portion 30 may further include a metal nanowire. The heater portion 30 may lower a driving voltage, i.e. a voltage applied to generate the Joule heat, thereby enabling quick and uniform heating over its entire portion. In detail, the metal nanowire may refer to a metal nanowire network positioned on one surface facing the skin, a surface opposite to the one surface or both the surfaces, with respect to the thin film of the transparent conductive oxide. The metal nanowire network may advantageously be positioned on a top surface of the thin film of the transparent conductive oxide, that is, the surface opposite to the one surface facing the skin.

The metal nanowire may use any metal that has excellent conductivity and ductility. For example, the metal of the metal nanowire may include silver (Ag), gold (Au), platinum (Pt), copper (Cu), aluminum (Al) or an alloy thereof, and is not limited thereto. In detail, the metal nanowire may have a surface resistance of 1 Ω/sq to 100 Ω/sq, and more specifically, 10 Ω/sq to 50 Ω/sq, and is not limited thereto. As a non-limiting example, the metal nanowire may be a silver nanowire (AgNW), and may be spin-coated on the thin film of the transparent conductive oxide.

The heater portion 30 as described above may have a thickness of 10 μm to 100 μm, specifically 30 μm to 80 μm, and more specifically 40 μm to 60 μm. Here, a thickness ratio (T1:T2) between the thickness (T1) of the transparent substance and the thickness(T2) of the transparent conductive oxide may be 100:1 to 1000:1, specifically 300:1 to 800:1, and more specifically the ratio of 400:1 to 600:1. In the above range, the heater portion 30 may have bending stiffness which allows the heater portion 30 to be used for a film-shaped heater, may not deteriorate its flexibility, and may prevent the heat energy, which is generated from the transparent conductive oxide, from being blocked by the transparent substance.

The heater portion 30 may heat the skin in contact with the oxygen sensing film 10 to a temperature of 40° C. to 50° C., specifically 42° C. to 46° C., and more specifically 44° C. to 45° C. In the above range, a human skin may be safe from burns even when heated for a long time. Here, as the blood flow is increased, the lipid layer of the skin, which obstructs an oxygen flow, may simultaneously have a loosen structure, thereby maximizing the partial pressure of oxygen supplied to the oxygen sensing film. Accordingly, it is possible to provide the sensor which may more reliably sense the oxygen partial pressure.

In one aspect of the present disclosure, as shown in FIG. 1, the flexible transcutaneous oxygen partial pressure sensor may further include the oxygen blocking film 20 positioned between the oxygen sensing film 10 and the heater portion 30, and having light transmittance.

The oxygen blocking film 20 stacked on the oxygen sensing film 10 is for minimizing the influence of the surrounding air when measuring the transcutaneous oxygen (TCPO$_2$) by using the sensor of the present disclosure, and may block the inflow of oxygen from the outside and prevent the outflow of oxygen supplied to the oxygen sensing film 10 from the skin, thereby maintaining the sensitivity of the oxygen sensing film. In detail, the oxygen blocking film 20 may use all conventional materials used to block the inflow of oxygen from the outside, and may preferably include polyvinylidene chloride (PVDC) having flexibility, excellent oxygen blocking power and light transmittance.

In one aspect of the present disclosure, as shown in FIG. 1, the flexible transcutaneous oxygen partial pressure sensor may further include the light shielding portion 80 stacked on the light detecting portion and blocking light.

The light shielding portion 80 may be made of an opaque material, and prevent light from being received from the outside into the transcutaneous oxygen partial pressure sensor of the present disclosure and prevent light inside the transcutaneous oxygen partial pressure sensor from emitting to the outside. Therefore, the light shielding portion 80 may prevent the sensing efficiency from being deteriorated by an external factor, and allow a more reliable result to be obtained. As a non-limiting example, the light shielding portion 80 may be a silicon tape (Si tape, black) having a thickness of 100 μm to 300 μm, and specifically a thickness of 150 μm to 250 μm.

In one aspect of the present disclosure, unlike as shown in the drawings, the light shielding portion 80 may further include a sealing film to protect the sensor from the external factor that may affect the measurement of the sensor, such as moisture.

The flexible transcutaneous oxygen partial pressure sensor of the present disclosure described above may be made of a flexible material, may be closely attached to the skin to measure oxygen partial pressure, and may thus sense oxygen more quickly.

Further, the sensor of the present disclosure may heat the skin by using a heating portion positioned between the oxygen sensing film and the light detecting portion, may increase the partial pressure of oxygen delivered to the sensor, and may thus accurately sense the oxygen partial pressure. Furthermore, the sensor of the present disclosure may use the micro-LED as the light source of its light detecting portion to stably sense the oxygen partial pressure even at a temperature higher than a body temperature, and may also be used repeatedly for a long time.

Figure 4:
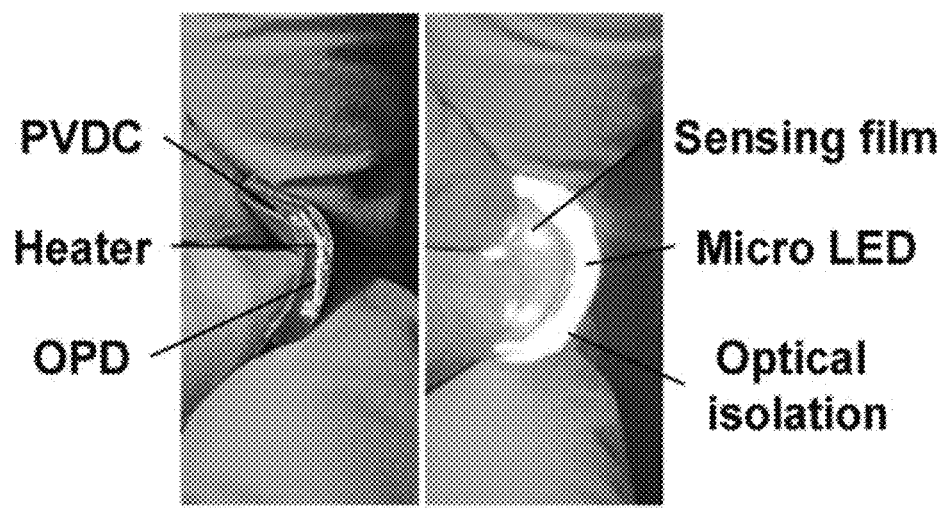
FIG. 4 is an optical image showing the flexibility of the flexible transcutaneous oxygen partial pressure sensor shown in FIG. 1.

FIG. 4 is an optical photograph of visual observation of the flexibility of the sensor shown in FIG. 1.

In detail, the oxygen sensing film of the sensor shown in FIG. 1 may be formed by containing platinum octaethylporphyrin (PtOEP) and titanium dioxide nanoparticles in a polystyrene (PS) solution, and the flexible substrate and transparent substrate of the light detecting portion may be formed of polydimethylsiloxane (PDMS). The heater portion may be formed by depositing indium tin oxide (ITO) having a thickness of 100 nm on a surface of the polyimide (PI) having a thickness of 50 μm. Referring to FIG. 4, it may be seen that the sensor of the present disclosure has flexibility and is operated even while being bent.

Figure 5:
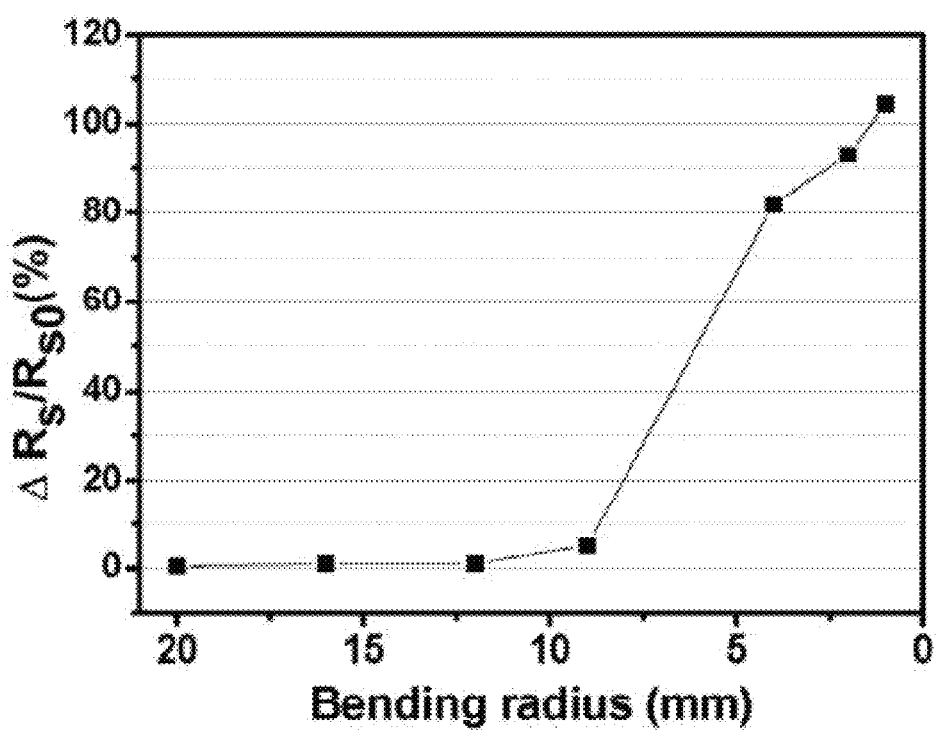
FIGS. 5 and 6 are graphs showing results of a bending test of the flexible transcutaneous oxygen partial pressure sensor shown in FIG. 1.
Figure 6:
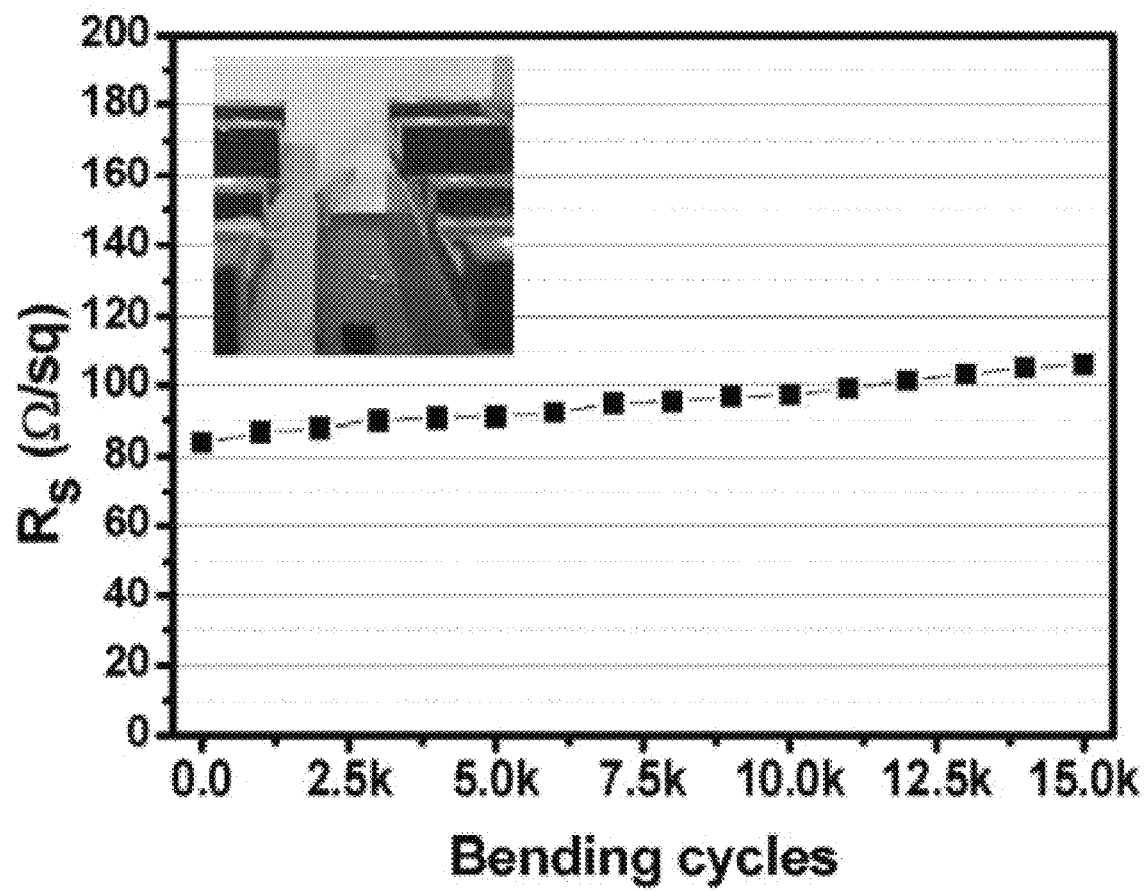

FIGS. 5 and 6 are graphs showing results of a bending test of the sensor shown in FIG. 1. FIG. 5 is a graph showing static bending at various bending radii, and FIG. 6 is a graph showing bending cycles at a bending radius of 9 mm.

Referring to FIGS. 5 and 6, the sensor of the present disclosure shows excellent bending stability. In particular, there is no significant change in the electric resistance of the heater portion even after being repeatedly bent 15,000 times.

FIGS. 7A to 7D each show a result of evaluating thermal stability of the heater portion of the flexible transcutaneous oxygen partial pressure sensor shown in FIG. 1.

Figure 7A:
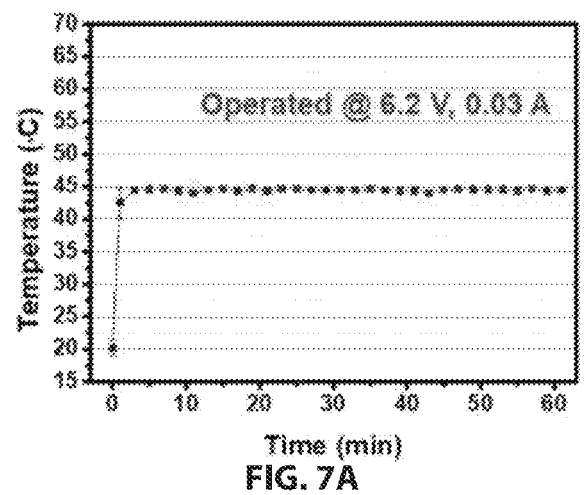
FIGS. 7A to 7D are a graph and images each showing a result of evaluating thermal stability of a heater portion of the flexible transcutaneous oxygen partial pressure sensor shown in FIG. 1.
Figure 7B:
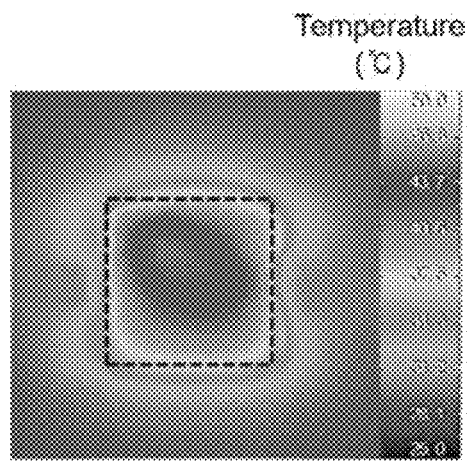
Figure 7C:
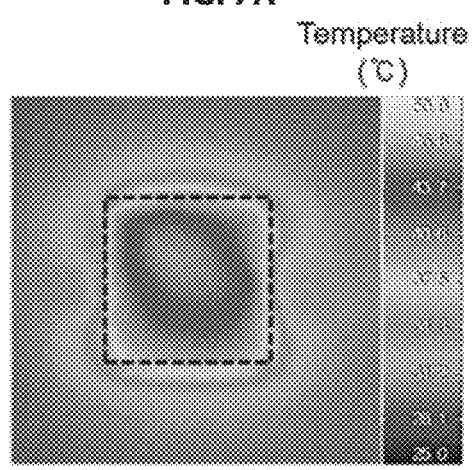
Figure 7D:
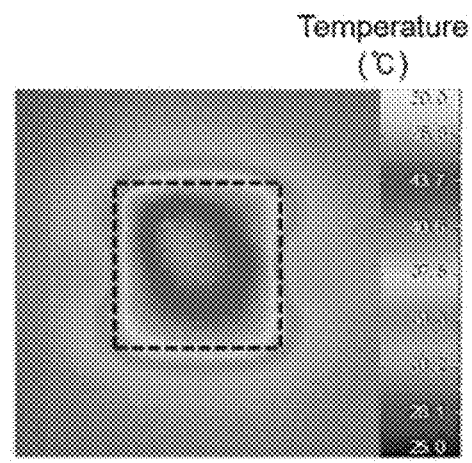

In detail, FIG. 7A shows a change in an average temperature over time of the heater portion having an applied voltage of 6V and a current of 0.03 A, and shows that the heater portion has a very stable heating characteristic. FIGS. 7B to 7D are images of the infrared rays (IR) of a temperature distribution in the heater portion of the flexible transcutaneous oxygen partial pressure sensor shown in FIG. 1. Referring to FIGS. 7B to 7D, it may be seen that the heater portion of the present disclosure shows a uniform and constant temperature over its entire surface area while 6.2V is continuously applied thereto for 60 minutes.

Figure 8:
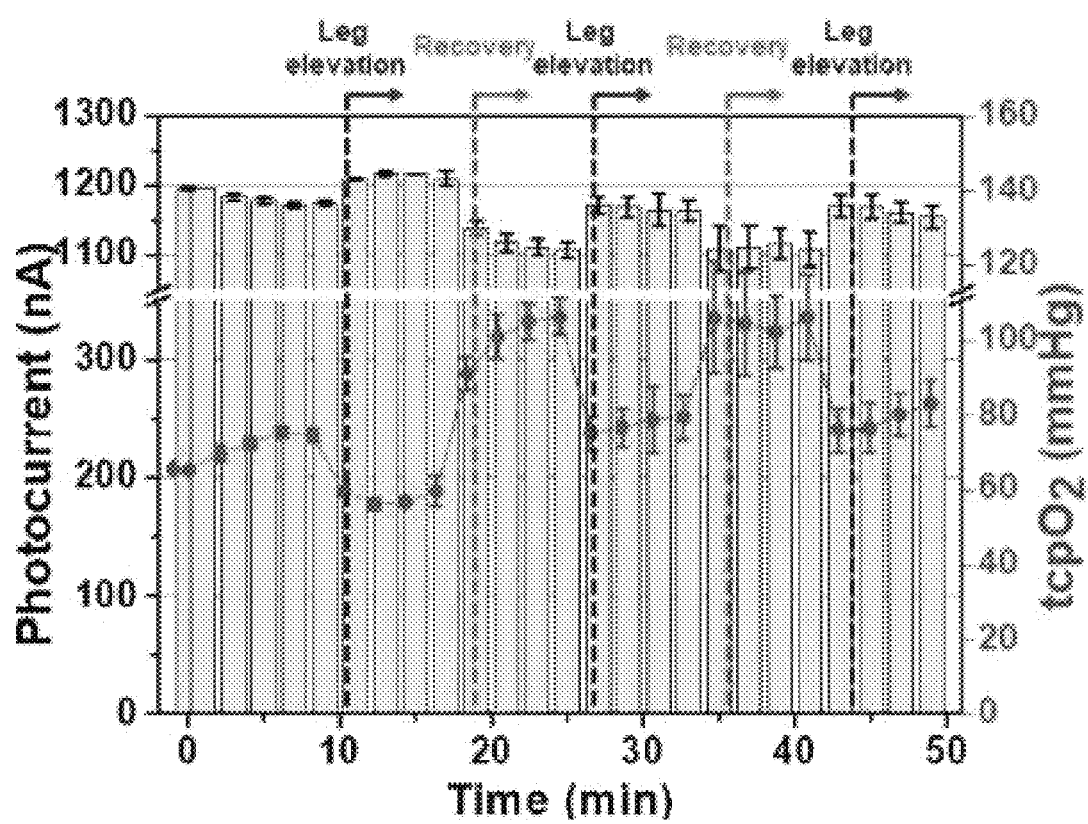
FIGS. 8 to 10 are graphs showing results of measuring photocurrent and transcutaneous oxygen ($TCPO_2$) according to measurement time flow when the flexible transcutaneous oxygen partial pressure sensor shown in FIG. 1 is attached to a human body.
Figure 9:
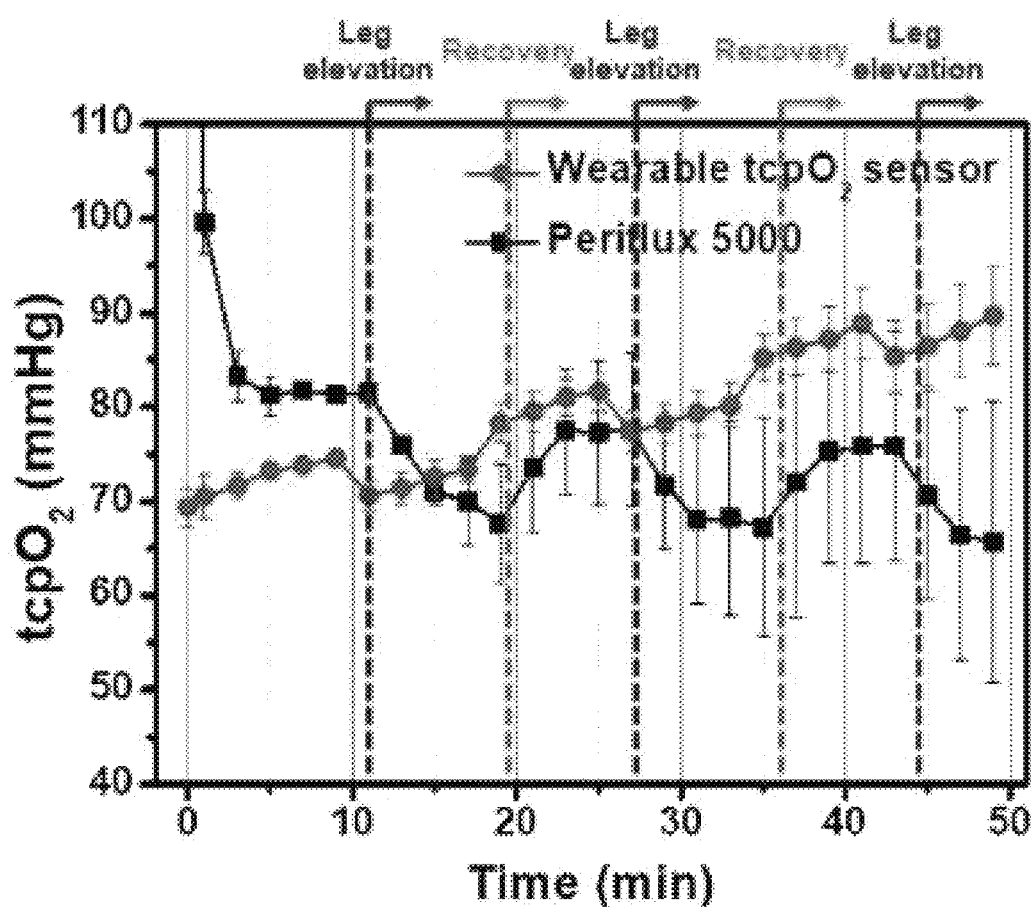
Figure 10:
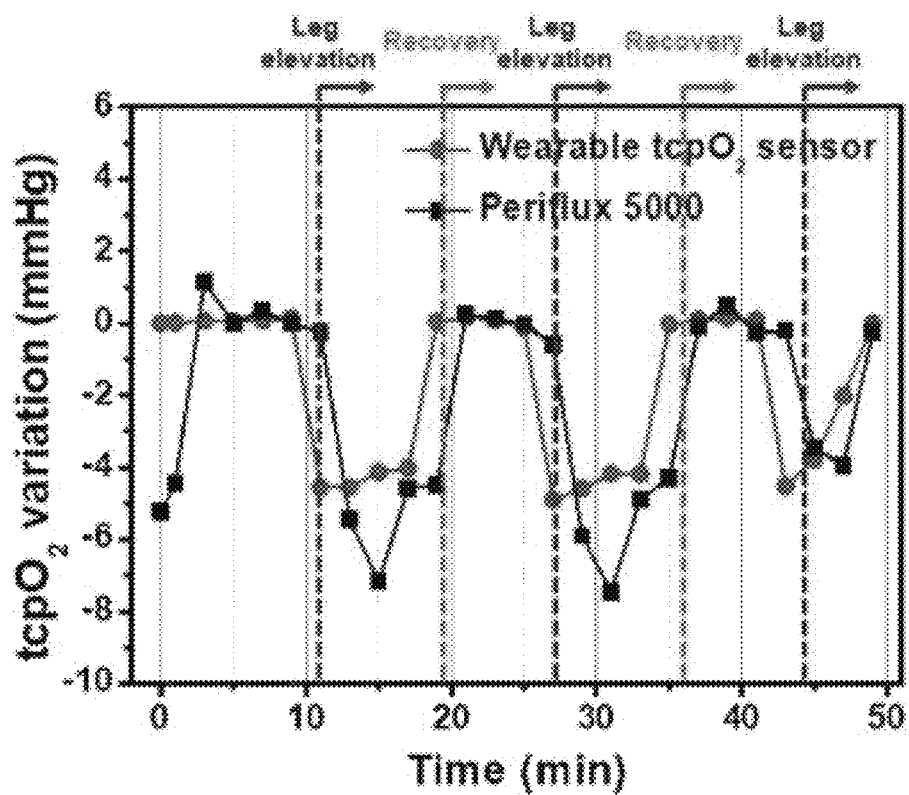

FIGS. 8 to 10 are graphs showing results of photocurrent and transcutaneous oxygen ($TCPO_2$) according to measurement time flow when the flexible transcutaneous oxygen partial pressure sensor shown in FIG. 1 is attached to a human body.

In detail, the flexible transcutaneous oxygen partial pressure sensor of the present disclosure and a commercially available PeriFlux5000 ($TCPO_2$ device, PF5040, PERIMED Co, SWEDEN) were attached to the ankle of a healthy adult having no clinical history of diabetes to measure the photocurrent and $TCPO_2$ values.

In more detail, each participant lay in a direction parallel to the ground in a laboratory where a room temperature was maintained at 25° C., and the flexible transcutaneous oxygen partial pressure sensor of the present disclosure was then attached to the participant's skin near his/her ankle in which the body hair had been removed. The photocurrent and $TCPO_2$ values were measured when the participant's leg was raised at an angle of 60° to the ground. After 8 minutes, the participant put his/her leg back down and rested for 8 minutes. The participant repeated the raising and lowering of his/her leg a total of three times.

The commercially available PeriFlux5000 was also attached to each of the same participants, and then the same motions were performed.

In detail, FIG. 8 is a graph showing the results of the photocurrent and the corresponding $TCPO_2$ of the sensor of the present disclosure according to the measurement time flow. Referring to FIG. 8, it may be seen that the values were reduced when the participant raised his/her leg, and the values were restored to its normal level when the participant lowered his/her leg again.

FIG. 9 is a graph showing a comparison of $TCPO_2$ results of the present disclosure sensor and the commercially available sensor, and FIG. 10 is a graph showing a comparison of their $TCPO_2$ results corrected by a data analysis program (Originlab corp).

Referring to FIGS. 9 and 10, it may be seen that the sensor of the present disclosure may measure $TCPO_2$ in a short time compared to the commercially available sensor. In addition, it may be seen that even when used for a long time, the sensor of the present disclosure shows higher accuracy and faster measurement speed than the commercially available sensor.

Figures 11A, 11B:
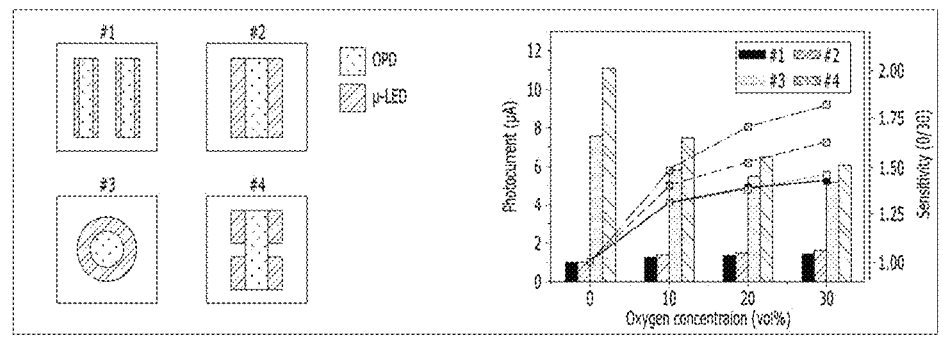
FIG. 11A shows diagrams each showing an arrangement of a light detecting portion of the flexible transcutaneous oxygen sensor shown in FIG. 1
FIG. 11B is a graph showing the result of measuring optical power based on the arrangement shown in FIG. 11A.

FIGS. FIG. 11A shows diagrams each showing an arrangement of the optical-photodiode (OPD) and the micro-light emitting diode (μ-LED) in the light detecting portion of the present disclosure and FIG. 11B is a graph showing comparison of the result values of photocurrents based on the arrangements shown in FIG. 11A. FIG. 11A shows schematic diagrams respectively showing four-type arrays of the OPD and μ-LED in #1 to #4. FIG. 11B is a graph showing a result of measuring the photocurrent by mounting each light detecting portion of arrays #1 to #4 on a gas flow cell, and then increasing oxygen concentration (vol %) from zero vol % to 30 vol % by 10 vol %. The photocurrent is transferred to LabVIEW software using a photodiode amplifier and a data acquisition (DAQ) module.

Referring to FIGS. 11A and 11B, it may be seen that high oxygen sensitivity is detected in the light detecting portion having array #4 in which four μ-LEDs are arranged at positions adjacent to each of the four edges of the rectangular OPD.

Figure 12A:
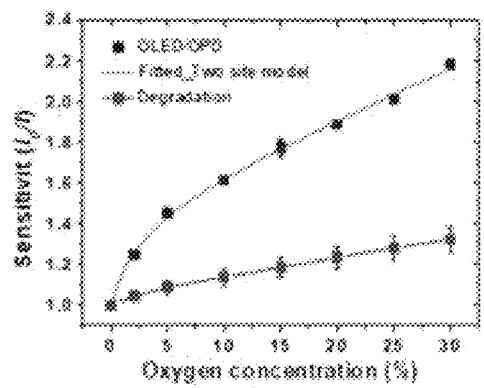
FIGS. 12A and 12B are graphs showing the sensitivity measurement and comparison of a conventional organic light emitting diode (OLED)-based sensor and a micro-light emitting diode (LED)-based sensor of the present disclosure.
Figure 12B:
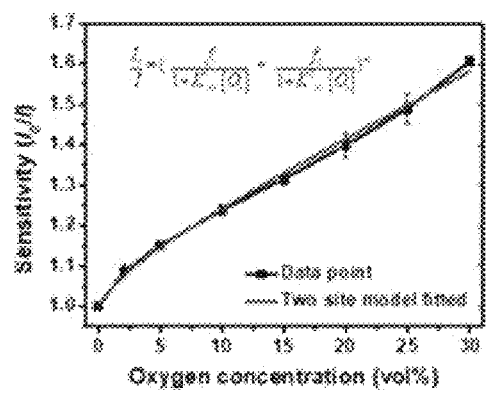

FIGS. 12A and 12B are Stern-Volmer graphs showing the sensitivity comparison of a conventional organic light emitting diode (OLED)-based sensor and the sensor of the present disclosure. FIG. 12A is a graph showing a result of measuring the sensitivity based on oxygen concentration of the conventional transcutaneous oxygen partial pressure sensor using the OLDE as its light source, and FIG. 12B is a graph showing a result of measuring the sensitivity based on the oxygen concentration of the flexible transcutaneous oxygen partial pressure sensor of the present disclosure. In detail, the sensitivity is expressed by the Stern-Volmer equation.

Referring to FIGS. 12A and 12B, it may be seen that the OLED-based conventional sensor shows degraded sensitivity due to its self-deterioration. However, the sensor of the present disclosure does not show degraded sensitivity, and thus has a higher sensitivity than the conventional OLED-based sensor.

Figure 13:
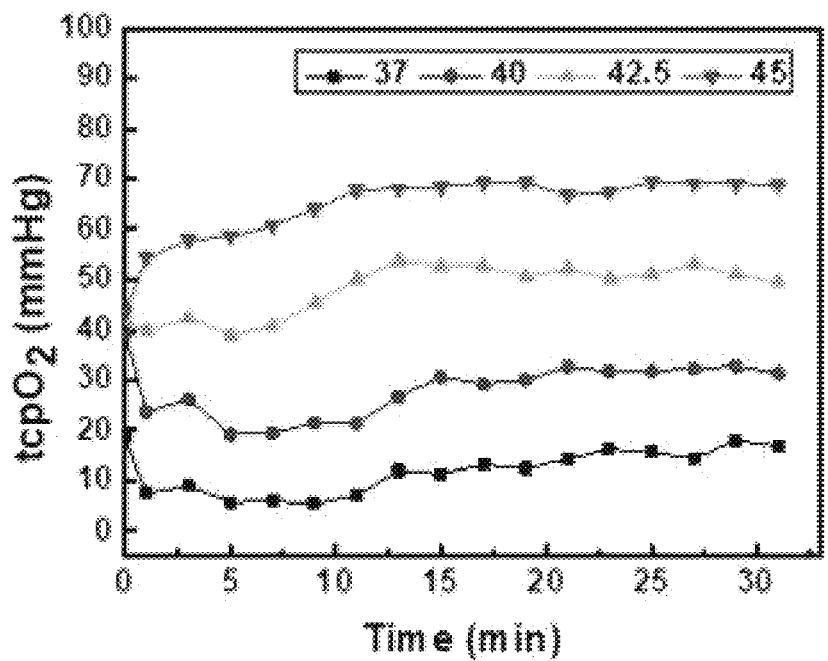
FIG. 13 is a graph showing oxygen partial pressure based on a skin temperature.

FIG. 13 is a graph showing a value of transcutaneous oxygen partial pressure measured on the skin of a clinical subject based on an increase in temperature, which is measured by a commercially available transcutaneous oxygen partial pressure sensor Periflux5000.

Referring to FIG. 13, it may be seen that the value of the transcutaneous oxygen partial pressure is linearly increased in proportion to the temperature. That is, it is possible to reliably sense the oxygen partial pressure because high oxygen partial pressure is generated when the skin is heated using the heater portion of the present disclosure.

The transcutaneous oxygen partial pressure sensor according to the present disclosure may heat the skin by using the heating portion, may increase the partial pressure of oxygen delivered to the sensor, and may thus accurately sense the oxygen partial pressure.

Further, the sensor of the present disclosure may use the micro-LED as the light source to stably sense the oxygen partial pressure even at a temperature higher than the body temperature, and may also be used repeatedly for a long time.

As described above, although the present disclosure is described with reference to specific matters, limited embodiments and drawings, they are provided only for assisting in the entire understanding of the present disclosure. Therefore, the present disclosure is not limited to the embodiments. Various modifications and changes may be made by those skilled in the art to which the present disclosure pertains from this description.

Accordingly, the spirit of the present disclosure should not be limited to the above-described embodiments, and the following claims as well as all modified equally or equivalently to the claims are intended to fall within the scope and spirit of the disclosure.

The invention claimed is:

1. A flexible transcutaneous oxygen partial pressure sensor comprising:
   an oxygen sensing film having one surface configured to be in contact with a skin;
   a light detecting portion including a light emitting portion which is positioned above a surface opposite to the one surface of the oxygen sensing film and includes a micro-light emitting diode (LED (μ-LED)), and a light-receiving portion which includes an organic-photodiode (OPD); and
   a heater portion positioned between the oxygen sensing film and the light detecting portion, and supplying thermal energy to the skin in contact with the oxygen sensing film,
   wherein the oxygen sensing film contains a polymer matrix, a phosphor and a scattering material, and
   wherein the scattering material increases a probability in which the light is absorbed by the phosphor to improve the sensing sensitivity of the oxygen sensing film.

2. The flexible transcutaneous oxygen partial pressure sensor of claim 1, wherein the heater portion includes a transparent conductor generating Joule heat.

3. The flexible transcutaneous oxygen partial pressure sensor of claim 2, wherein the heater portion includes a transparent conductive oxide.

4. The flexible transcutaneous oxygen partial pressure sensor of claim 3, wherein the heater portion has a thickness of 10 μm to 100 μm.

5. The flexible transcutaneous oxygen partial pressure sensor of claim 1, wherein the heater portion is configured to heats the skin in contact with the oxygen sensing film to a temperature of 40° C. to 50° C.

6. The flexible transcutaneous oxygen partial pressure sensor of claim 1, wherein the light detecting portion includes the light emitting portion stacked on the heater portion and the light-receiving portion stacked above the light emitting portion, and further includes an optical filter positioned between the light emitting portion and the light-receiving portion.

7. The flexible transcutaneous oxygen partial pressure sensor of claim 1, wherein the light emitting portion includes a transparent substrate and an array in which micro-LEDs are arranged on the transparent substrate,
   the transparent substrate being made of a flexible light-transmitting material.

8. The flexible transcutaneous oxygen partial pressure sensor of claim 1, wherein the organic-photodiode (OPD) includes an electron transport layer including polyethyleneimine ethoxide and cesium carbonate.

9. The flexible transcutaneous oxygen partial pressure sensor of claim 8, wherein the electron transport layer has a first region including polyethyleneimine ethoxide and a second region doped with the first region and including cesium carbonate.

10. The flexible transcutaneous oxygen partial pressure sensor of claim 1 further comprising an oxygen blocking film positioned between the oxygen sensing film and the heater portion, and having light transmittance.

11. The flexible transcutaneous oxygen partial pressure sensor of claim 10, wherein the oxygen blocking film includes polyvinylidene chloride.

12. The flexible transcutaneous oxygen partial pressure sensor of claim 1 further comprising a light shielding portion which is stacked on the light detecting portion and blocks light.

13. The flexible transcutaneous oxygen partial pressure sensor of claim 1, wherein the scattering material includes a titanium dioxide particle.

14. The flexible transcutaneous oxygen partial pressure sensor of claim 13, wherein the titanium dioxide particle has a rutile structure.

* * * * *